United States Patent [19]

Staubli

[11] Patent Number: 5,538,428
[45] Date of Patent: Jul. 23, 1996

[54] PACKING DELIVERY SYSTEM FOR DENTAL IMPLANT AND METHOD

[75] Inventor: Peter E. Staubli, San Carlos, Calif.

[73] Assignee: Attachments International, San Mateo, Calif.

[21] Appl. No.: 223,486

[22] Filed: Apr. 5, 1994

[51] Int. Cl.⁶ ................................................. A61C 8/00
[52] U.S. Cl. ............................................ 433/173; 206/63.5
[58] Field of Search .................................. 433/172, 173, 433/174; 206/63.5, 338, 339, 368, 438

[56] References Cited

U.S. PATENT DOCUMENTS

| | | | |
|---|---|---|---|
| 4,856,994 | 8/1989 | Lazzara et al. | 433/173 |
| 4,960,381 | 10/1990 | Niznick | 433/174 |
| 5,062,800 | 11/1991 | Niznick | 433/173 X |
| 5,281,140 | 1/1994 | Niznick | 433/173 X |
| 5,312,254 | 5/1994 | Rosenlicht | 433/173 |
| 5,322,443 | 6/1994 | Beaty | 433/173 X |
| 5,368,160 | 11/1994 | Leuschen et al. | 206/339 |

*Primary Examiner*—Christopher A. Bennett
*Attorney, Agent, or Firm*—Townsend and Townsend and Crew; Kenneth R. Allen; Darin J. Gibby

[57] ABSTRACT

A packaging and delivery system and accompanying method for a dental attachment allows delivery of a dental implant from a storage device directly to a patient without handling the dental implant. The dental implant is removably connected to an implant mount, which is connected to an implant mount carrier. The implant mount carrier is received into an open end of a storage vial such that the implant mount and the implant are housed within the vial. To deliver the implant to the patient, the implant is removed from the storage vial via the implant mount carrier and positioned at the desired position on the patient. A torque is then applied to the implant mount carrier to screw the implant into the patient. The implant mount carrier is then removed and further torque can be applied to the implant mount. Once the implant is secured, the implant mount is removed from the implant. A cover screw, connected to a cover screw driver, housed within a second vial can then be removed from the vial via the cover screw driver and inserted into the top of the implant. This implant system is a "complete" or advanced delivery system because it includes all parts needed to remove and place the implant. Another "minimum" or economical delivery system is also provided which contains the implant and the cover screw, but is only designed for use with a separate and previously obtained implant mount, implant mount carrier, and screw driver.

42 Claims, 9 Drawing Sheets

PACKING DELIVERY SYSTEM FOR DENTAL IMPLANT AND METHOD

BACKGROUND OF THE INVENTION

1. Field of the Invention

The present invention relates to a system for packing and delivering a dental attachment. In particular, the invention relates to a dental implant delivery system, i.e. the system for delivering a dental implant and associated parts to a patient from a storage device housing the implant and associated parts.

Dental implants are widely known and used in the field of dentistry as a dental prosthetic. The known delivery systems suffer from a number of drawbacks. For example, the current practice involves opening the package containing the dental implant and placing the implant on a surface or a tray until required by the surgeon. The implant must be picked up by the surgeon, usually by the use of fingers or tweezers, where it is attached to a mounting device. Using the mounting device, the surgeon positions the implant appropriately so that it may be inserted into the patient.

This technique has substantial risks. The implant is in a potentially unsterile environment. The need for handling of the implant before insertion into the patient increases the chances for contamination of the implant. Furthermore, the delivery process is cumbersome, involving taking the implant out of the packaging, grasping the implant with a tool or hand, and then placing the implant on a mounting device in order to insert the implant into the patient.

It would therefore be desirable to provide a packaging and delivering system whereby a surgeon can remove the implant from the packaging and place the implant without having to touch the implant thereby potentially affecting its sterility. Further, the packaging and delivery system should provide the surgeon with an easy way to take the implant from the packaging and to insert it within the patient.

2. Description of Background Art

U.S. Pat. No. 4,960,381 describes one type of screw-type dental implant typical of those used in the art.

SUMMARY OF THE INVENTION

A dental implant delivery system has an implant carrier that is removably attached to a dental implant, and the implant carrier is configured so that it is removably attached to a storage container. The storage container may be any size or shape as long as the container is able to house the implant and to maintain sterility. Preferably, the implant carrier has a tab extending therefrom which is insertable into an opening of the storage container.

In one embodiment, the tab is circular in cross section and the storage container is a housing with an open end, a closed end, and a cylindrical interior for receiving the implant carrier. The implant carrier has a shaft that is insertable into the bottom end of the implant. Preferably, the shaft is cylindrical and can be press-fit within a corresponding cylindrical opening of the bottom end of the implant. Alternatively, the shaft can be threaded and joined with a threaded opening at the bottom end of the implant. With this embodiment, the implant may be removed from the storage container by simply grasping the implant carrier and removing it from the storage container. This allows the implant to be removed from the storage container without undue contact with external sources of contamination.

In another embodiment of the dental implant delivery system, a cover screw is provided in the storage container that can be received into the top end of the dental implant. The cover screw is housed in a cover screw carrier and located between the dental implant and the closed end of the storage container. In this embodiment, both the implant and the cover screw may be removed from the storage device and the implant may be delivered to the patient with minimal risk of contamination.

In yet another embodiment, the storage device has two open ends opposite each other. The implant carrier is attached to one of the open ends and the cover screw carrier is attached to the opposite end to completely enclose the dental implant and the cover screw within the storage device.

Once the dental implant is removed from the storage device by the implant carrier, it can be prepared for insertion into the patient by attaching an implant mount and an implant mount carrier. The implant mount carrier assists in this process by allowing the implant to be securely held at its bottom end while attaching the implant mount and the implant mount carrier at its top end. The dental implant can then be removed from the implant carrier and delivered into the patient with minimal risk of contamination. Further, a cover screw driver can be inserted into the cover screw to remove the cover screw from the cover screw carrier and delivered to the patient thereby minimizing the risk of contamination of the cover screw.

In another aspect of the present invention, a dental delivery system for delivering a system of dental parts is provided. According to this aspect of the invention, a dental implant is removably attached to an implant mount which in turn is removably attached to an implant mount carrier. The implant mount carrier is in turn removably engaged with a first storage device such that the implant is enclosed within an interior portion of the first storage device. The implant can be removed from the first storage device by the implant mount carrier and delivered to the patient.

In another aspect, a cover screw for the implant is provided. The cover screw is attached to a cover screw driver which is removably engaged to a second storage device such that the cover screw is enclosed within an interior portion of the second storage device. This configuration allows the cover screw to be removed from the second storage device by the cover screw driver.

In another embodiment of the invention, an apparatus in kit form is provided for delivering dental parts from a single storage device a patient. The kit contains a dental implant having a top end and a bottom end, an implant mount having a top end and a bottom end (the bottom end of the implant mount being removably attached to the top end of the dental implant), an implant mount carrier engaged with the top end of the implant mount, a cover screw for the implant, and a cover screw driver attached to a head of the cover screw. The storage device has an open interior portion and two open ends. The implant mount carrier is removably engaged with one of the open ends such that the dental implant is enclosed within the interior portion of the storage device. The cover screw driver is removeably engaged with the other open end such that the cover screw is also enclosed within the interior portion of the storage device.

A method for delivering a set of dental parts from the storage device to a patient is also provided. According to this method, the implant is removed from the storage device by grasping an implant carrier which is attached to a bottom end of the implant. An implant mount is attached to a top end of the implant and an implant mount carrier is attached to the implant mount. The implant carrier is then removed from the implant thereby making the implant available for insertion into the patient. A dental implant cover screw that is housed in a cover screw carrier is also removed from the storage device. A cover screw driver is then attached to the cover screw, and the cover screw is removed from the cover screw carrier by the cover screw driver. The cover screw is then delivered to the dental implant.

In another embodiment, the dental implant is removably connected to an implant mount and the implant mount is removably connected to an implant mount carrier. The implant is removed from the storage device by grasping the implant mount carrier. The implant is then positioned at the desired spot on the patient and a torque is applied to the implant mount carrier to screw the implant into the patient. Once inserted, the implant mount carrier and the implant mount are removed from the implant. Alternatively, a torque may be applied to the implant mount to further secure the implant after removal of the implant mount carrier. A cover screw driver attached to a cover screw that is housed in a second storage device is attached to the dental implant by grasping the cover screw driver and separating it from the second storage device. The cover screw driver is then used to deliver the cover screw to the dental implant. The cover screw is then torqued into the dental implant by the cover screw driver, and the cover screw driver is removed. The system of the present invention thus reduces or eliminates the need for handling and manipulation thereby increasing efficiency and reducing the possibility of contamination.

The invention will be better understood upon reference to the following detailed description in connection with the accompanying drawings.

DETAILED DESCRIPTION OF THE SPECIFIC EMBODIMENTS

Figure 1A:
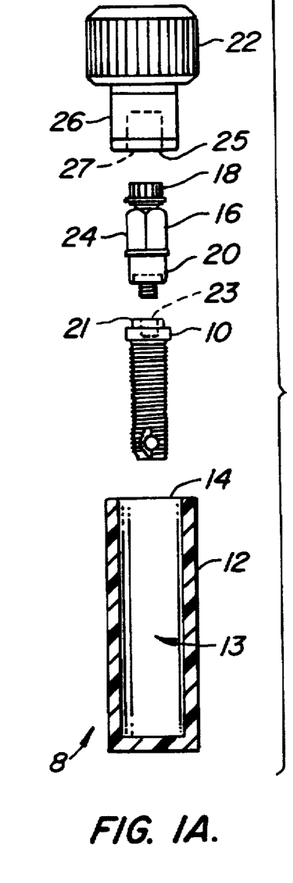
FIG. 1A is an exploded side view of a dental implant, an implant mount, and an implant mount carrier that are included in the "complete" or advanced dental delivery system according to the present invention.
Figure 1B:
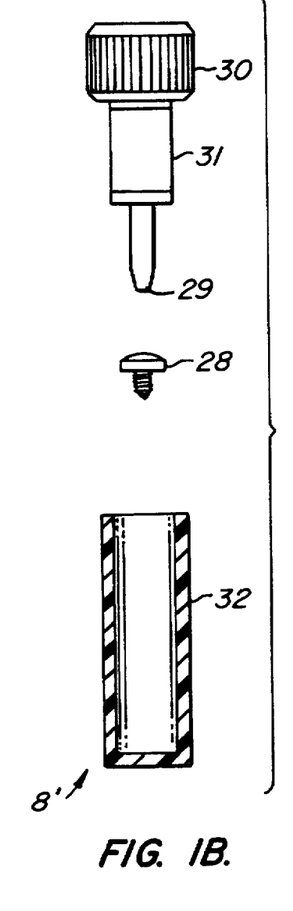
FIG. 1B is an exploded side view of a cover screw and a cover screw driver that are included in the "complete" or advanced dental delivery system according to the present invention.

Turning to FIGS. 1A and 1B, a "complete" or advanced dental delivery system is illustrated. The system is complete because it contains all the parts necessary to remove an implant from a storage container and to place it within the patient. The "complete" or advanced system includes an implant storage system 8 and a cover screw storage system 8'. The implant storage system 8 includes a dental implant 10 of conventional design that is stored within a vial 12. The dental implant 10 is typically constructed of titanium or other bio-compatible material to enable the patient's bone to adhere to the implant 10 when inserted into the jaw of the patient. The vial 12 has a cylindrical interior 13 with an open top portion 14 so that the dental implant 10 may placed within the vial 12 for storage. The vial 12 can be constructed of any material which can maintain a sterile environment within the vial 10, and is preferably constructed from transparent plastic, glass or the like.

An implant mount 16 is removably attached to the dental implant 10. The implant mount 16 is used to mount the implant 10 into the patient as described hereinafter. The implant mount 16 is preferably constructed of titanium, composites or stainless steel or like noncorrosive material, and can be reusable in mounting other implants as discussed below. The implant mount 16 has a screw 18 slidably mounted within a generally cylindrical sleeve 20. The screw 18 is configured to screw into a threaded female portion 23 at the top of the dental implant 10. Preferably, the head of the screw 18 is configured to that the screw may be torqued by hand. As the screw is tightened into the implant 10, the sleeve 20 engages with an engagement surface 21 at the top of the dental implant 10. Preferably, the engagement surface 21 is hexagonal and mates with a corresponding hexagonal female portion of the sleeve 20. The sleeve 20 is configured to have an outer surface that can easily mate with a wrench or other torquing device. Preferably, the outer surface is square so that a conventional wrench can be used to apply a torque to the implant mount 16 thereby torquing the engaged dental implant 10 into the patient.

An implant mount carrier 22 is configured to slide over the top of implant mount 16 and engage with the middle portion 24 of the implant mount 16. According to the invention, the implant mount carrier 22 is used to both deliver the implant 10 from the storage device 12 and insert the implant 10 into the patient as described below. The implant mount carrier 22 is preferably made of plastic but can be constructed from any suitable material, and can be reused. The implant mount carrier 22 has a female interior portion 27, preferably square, at a bottom end 25 for receiving the middle portion 24 of the implant mount 16. The bottom end 25 of implant mount carrier 22 also has a tabular portion 26. The tabular end 26 is preferably round in cross section so that it can be received within the top portion 14 of the vial 12, preferably by a press fit. Alternatively, the tabular end 26 may be threaded and screwed into a threaded top portion 14 of the vial 12.

When packaged, the implant 10 is attached to the implant mount 16 which in turn is attached to the implant mount carrier 22. The implant mount carrier 22 is engaged with the vial 12 by the tabular portion 26 forming a cover so that the implant 10 and the implant mount 16 are enclosed within the vial 12. This configuration allows for easy removal of the dental implant 10 from the vial 12 by simply grasping the implant mount carrier 22 and axially sliding it from the vial 12. Since the implant 10 is connected to the implant mount carrier 22 via the implant mount 16, the implant 10 is removed from the vial 12 along with the implant mount carrier 22.

Once removed from the vial 12, the implant 10 is delivered directly to the patient via the cover mount carrier 22 without being touched. The implant 10 is inserted into the patient by placing the implant 10 into a pre-formed hole in the patient and torquing the implant mount carrier 22 to screw the implant 10 into the patient. To further secure the implant 10 into the patient, the implant mount carrier 22 is removed from the implant mount 16 by grasping the implant mount carrier 22 and sliding the implant mount carrier 22 in an upward direction until the implant mount carrier 22 is removed from the implant mount 16. The implant mount 16 is then further torqued by placing a wrench or the like about the middle portion 24 and applying a force. The implant mount 16 is then removed from the implant 10 by turning the screw 18 and removing the implant mount 16.

The "complete" or advanced dental delivery system also has a cover screw storage system 8' as shown in FIG. 1B. The system 8' has a cover screw 28 that is insertable into the top of the implant 10 after the implant mount 16 has been removed. Along with the cover screw 28 is a cover screw driver 30 which can be reused with other cover screws. When packaged, an engaging portion 29 of cover screw driver 30 is attached to the top of cover screw 28, preferably by a press fit. The engagement portion 29 can be configured in any manner so long as it is capable of both attachment to the cover screw 28 and transferring a torque provided by the cover screw driver 30 to the cover screw 28. Preferable configurations include square, tapered or hexagonal. The cover screw driver 30 will be engaged with a second vial 32 in a manner similar to that just discussed in connection with the implant mount carrier 22. The second vial 22 can be configured to be identical to the first vial 12, and the cover screw driver 30 can have a tabular portion 31 with a cross section identical to the top portion 26 of the implant mount carrier 22 so that the cover screw driver 30 can be attached to the second vial 32. The cover screw 28 is removed from the second vial 32 by simply removing the cover screw driver 30 from the vial 32. Once removed, the cover screw 28 is delivered to the patient via the cover screw driver 30 and inserted into the implant 10. Since the cover screw driver 30 is press fit with the cover screw 28, the cover screw driver 30 can easily be removed from the inserted cover screw 28 by pulling the cover screw driver 30 from the cover screw 28.

Figure 1C:
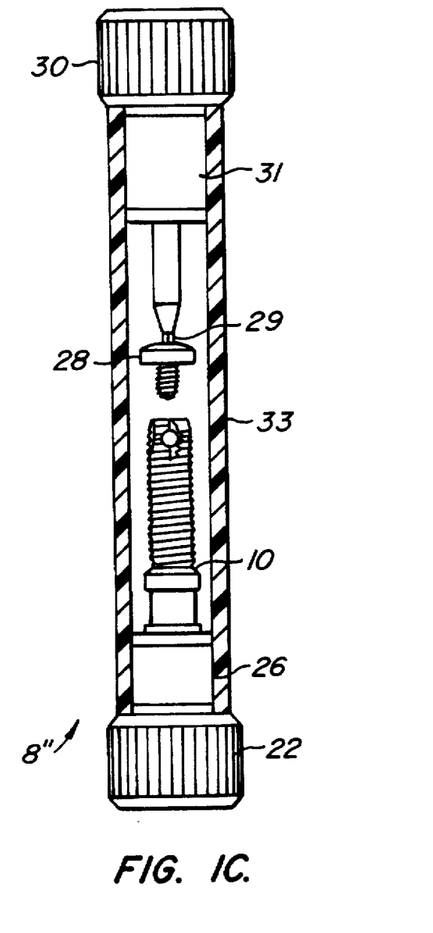
FIG. 1C is a side view showing the parts of FIGS. 1A and 1B combined and stored within a single storage device.

In FIG. 1C, the systems 8 and 8' of FIGS. 1A and 1B are combined into a single system 8" which uses a single vial 33. The vial 33 has two open ends and can be formed by removing the closed ends of vials 12 and 32 and joining vials 12 and 32 together. The system 8" combines substantially the identical elements of FIGS. 1A and 1B so that the cover screw 28 and the dental implant 10 can be stored within the single vial 33.

Figure 2A:
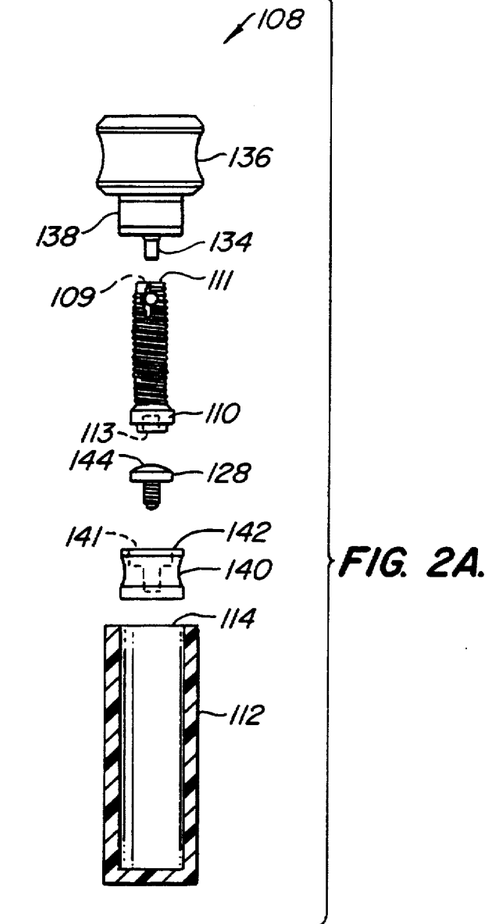
FIG. 2A is an exploded side view of a "minimum" or economical dental delivery system according to the present invention.
Figure 2B:
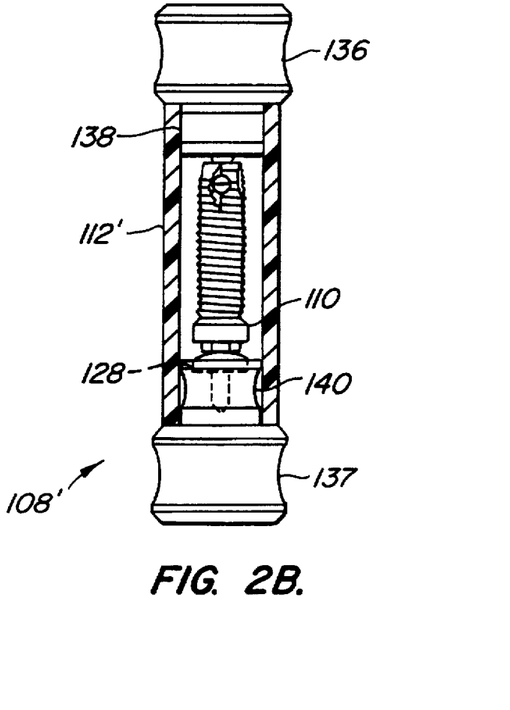
FIG. 2B illustrates the economical delivery system of FIG. 2A with a handle added to the cover screw carrier according to the present invention.

The "complete" or advanced delivery system of FIGS. 1A–C therefore allow a surgeon to remove both the dental implant 10 and the cover screw 28 from a storage vial(s) without having to unduly touch or handle either the implant 10 or the cover screw 28. As illustrated in FIG. 2A, the invention also provides a "minimum" or economical delivery system 108 to be used in conjunction with the "complete" or advanced delivery system. As discussed in connection with FIGS. 1A and B above, implant mounts, implant mount carriers, and cover screw drivers can be reused to reduce expenses to the patient. However, the reuse of these components with a new implant and/or cover screw can lead to the same increased risks of contamination and inconvenience to the surgeon as discussed above in connection with FIGS. 1A and B. Specifically, the implant and cover screw are removed from the packaging and then extensively handled in order to attach the implant mount, the implant mount carrier, or the cover screw driver. In order to reduce or eliminate these problems while maintaining the capability of reusing separately and previously obtained implant mounts, implant mount carriers, and screw drivers, the economical delivery system 108 shown in FIG. 2A–B is provided.

The economical delivery system 108 has an implant 110 which can be configured to be identical to the implant described in FIG. 1A. The implant 110 has an opening 109 in a bottom portion 111 for receiving an extending portion 134 of an implant carrier 136. The extending portion 134 of implant carrier 136 is preferably a cylindrical or tapered metal, composite, plastic or the like shaft (with or without threads) that mates with a corresponding opening 109 in the bottom portion 111 of the implant mount 110. The extending portion 134 is preferably press fit into the implant mount 110 to securely connect the two parts. Alternatively, the extending portion 134 can be threaded and screwed into implant 110. The implant carrier 136 has a tabular portion 138 which is engagable with a top portion 114 of a vial 112 similar to the system discussed in connection with FIGS. 1A and B. The vial 112 can be configured to be identical to the vials discussed in FIGS. 1A and B, and the tabular portion 114 the same cross-section as the tabular portion of the implant mount carrier described in FIG. 1A, so that when the vial 112 is engaged with the implant carrier 136, a cover is formed over the vial 112 thereby securing the implant 110 within the vial 112.

The economical delivery system 108 can also have a cover screw 128 housed in a cover screw carrier 140. The cover screw 128 is used to cover a female portion 113 of the implant 110 after insertion into the patient and can be configured to be identical to the cover screw described in FIG. 1B. The cover screw carrier 140 is preferably substantially cylindrical so that it can he housed within the vial 112. The cover screw carrier 140 is preferably constructed of plastic or other easily machinable material with an opening 141 in a top end 142 for receiving the cover screw 128. The opening 141 will preferably be configured to mate with the shape of the cover screw 128. In this manner, the cover screw 128 can be placed within the cover screw carrier 140 by being screwed into the opening 141, or alternatively, can be press fit within the opening 141. When housed within the cover screw carrier 140, a head 144 of the cover screw 128 is countersunk below the top end 142 to reduce the possibility of contamination when the cover screw carrier 140 is removed from the vial 112 as discussed below. When packaged in the vial 112, the cover screw carrier 140 (housing the cover screw 128) is positioned between a bottom end 146 of the vial 112 and the implant 110. The cover screw carrier 136 is preferably made of plastic so that it may easily be machined. The cover screw carrier 136 can be provided in a variety of differing lengths so that the when packaged, the implant 110 is adjacent the cover screw carrier without any excess space in the vial 112.

To deliver the implant 110 and the cover screw 128 to the patient, the implant carrier 136 is grasped and removed from the vial 112. Once removed, an implant mount (not shown) and an implant mount carrier (not shown) are attached similar to that described in FIG. 1A. The implant carrier 136 is instrumental in this process by allowing the implant 110 to be securely held at its bottom end while having the top end free to attach the implant mount and the implant mount carrier. Further, the implant mount and the implant mount carrier can be attached to the implant 110 without requiring the surgeon to touch the implant 110. Once attached, the implant carrier 136 is removed by pulling or unscrewing the implant carrier 136 from the implant 110, and the implant 110 is then delivered to the patient via the implant mount carrier as described in connection with FIG. 1A. The cover screw carrier 140 is removed from the vial 112 by tipping the vial 112 and allowing the cover screw carrier 140 to slide out from the vial 112. Once removed, a cover screw driver (not shown) is attached to the cover screw 128 by a press fit as described in FIG. 1B. The cover screw 128 is then unscrewed and/or lifted from the cover screw carrier 140 via the cover screw driver and delivered to the implant 110 as described in connection with FIG. 1B.

In FIG. 2B, an economical delivery system 108' is shown. The system 108' is substantially identical to system 108 shown in FIG. 2A except that both ends of vial 112' are open. Also a handle 137 is attached to the cover screw carrier 140. This embodiment allows the cover screw carrier 140 to be removed from the vial 112' by grasping the handle 137 and separating the cover screw carrier 140 from the vial 112'.

Figure 3A:
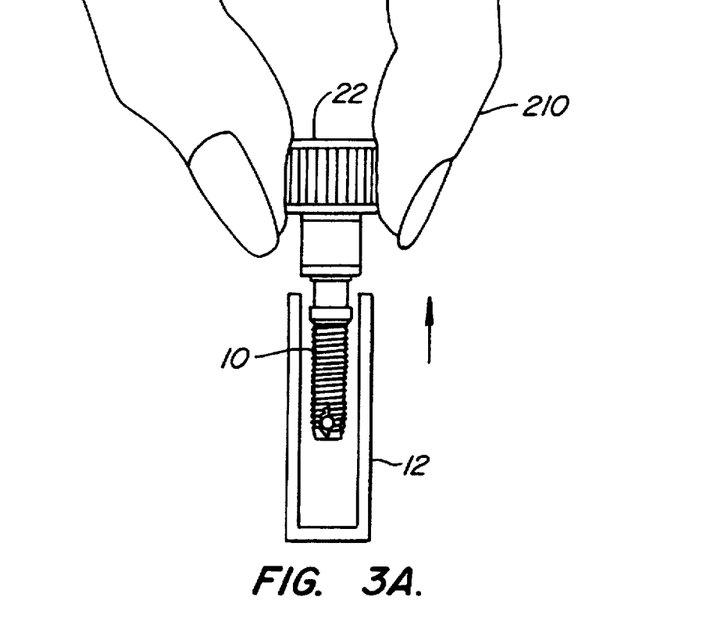
FIGS. 3A–G illustrate a method for delivering a dental implant and a cover screw that are housed within separate storage vials to a patient according to the present invention.
Figure 3B:
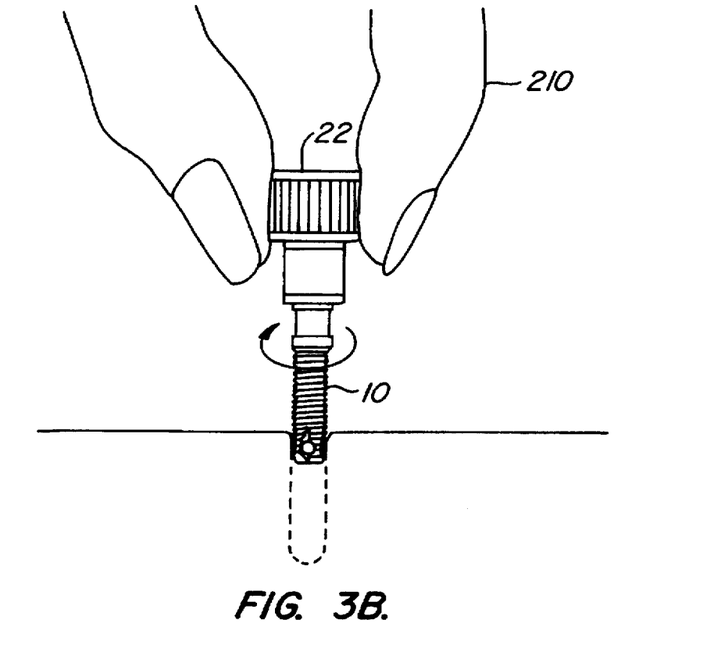

A method for delivering the dental implant and the cover screw of FIGS. 1A and B is illustrated in FIGS. 3A–G. According to the method, the implant mount carrier 22 is grasped with one hand 210 while holding the vial 12 with the other hand (not shown) as illustrated in FIG. 3A. The implant mount carrier 22 is then pulled from the vial 12. The vial 12 can then be discarded. The surgeon is then able to transport the dental implant 10 to the patient via the implant mount carrier 22 to the patient's jaw without having to touch the dental implant 10. The dental implant 10 is then inserted into the patient as shown in FIG. 3B.

Figure 3C:
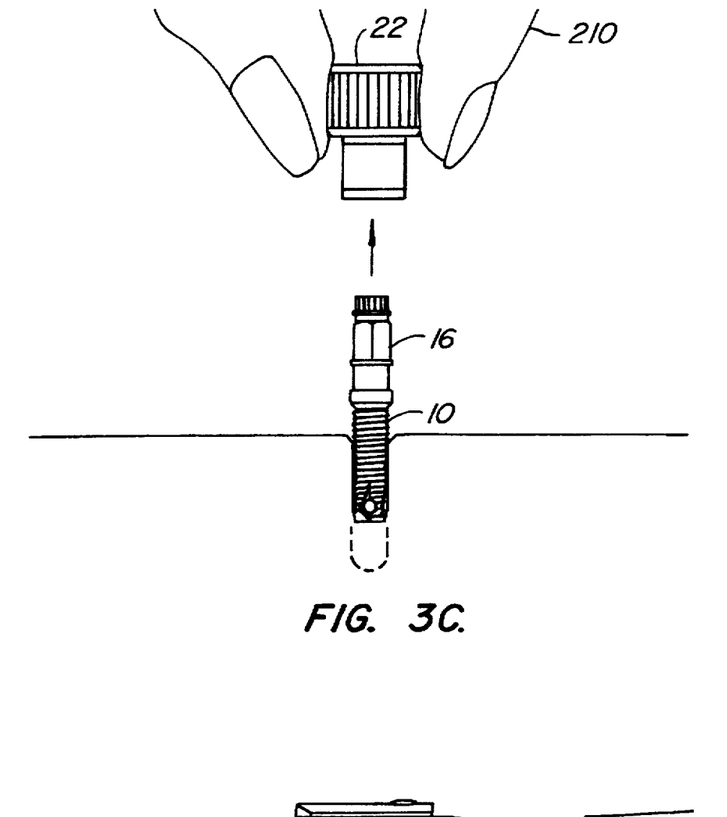
Figure 3D:
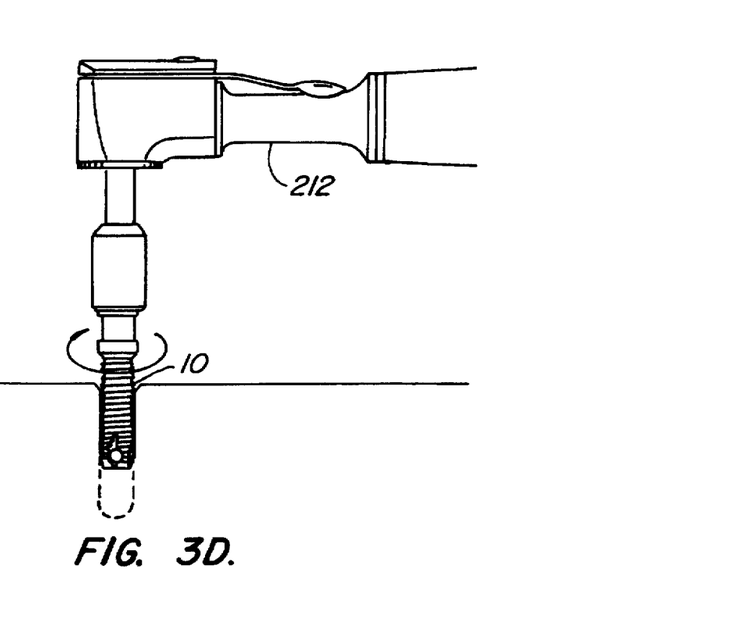

Once the implant 10 is in the patient's jaw, the implant mount carrier 22 is removed from the implant mount 16 as shown in FIG. 3C. A torquing instrument 212 is then attached to the implant mount 16 to torque the implant 10 into the patient's jaw as shown in FIG. 3D.

Figure 3E:
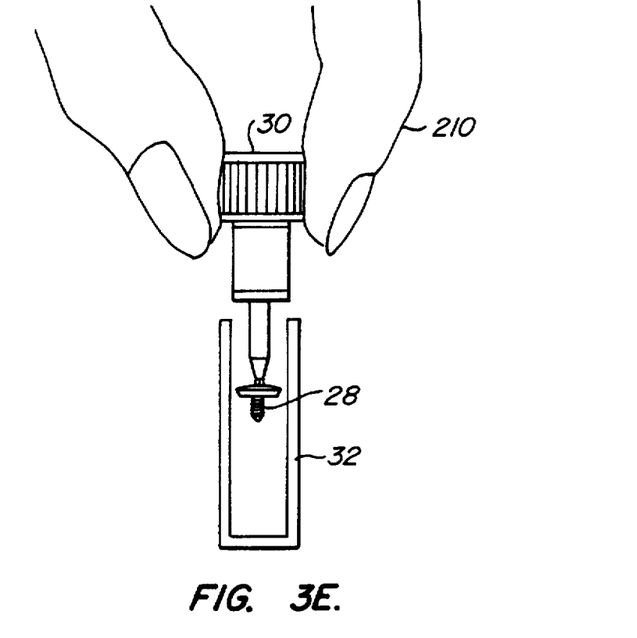
Figure 3F:
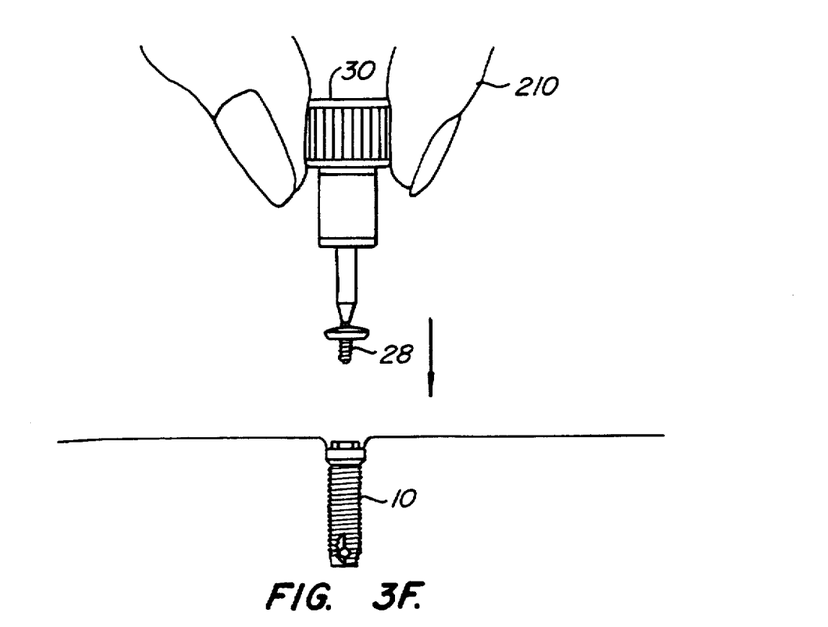
Figure 3G:
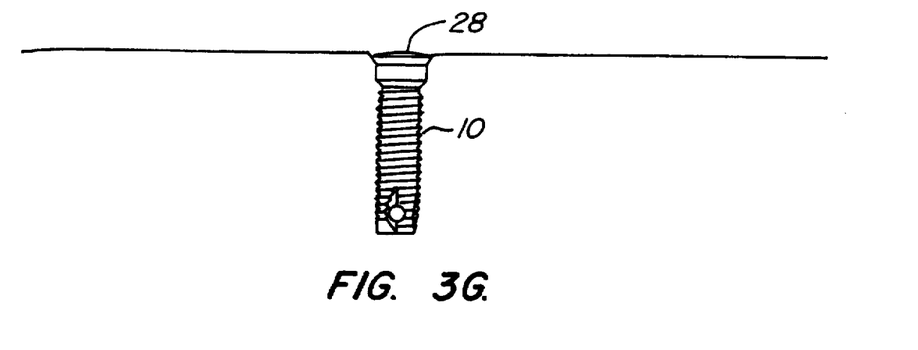

Once the dental implant 10 is inserted, the cover screw 28 is removed from the vial 32 as shown in FIG. 3E. This is done by grasping the cover screw driver 30 with one hand 210 and the vial 32 with the other hand (not shown). The cover screw driver 30 is then pulled from the vial 32. The vial 32 can then be discarded and the cover screw 28 inserted into the implant 10 as shown in FIGS. 3F and 3G.

Figure 4A:
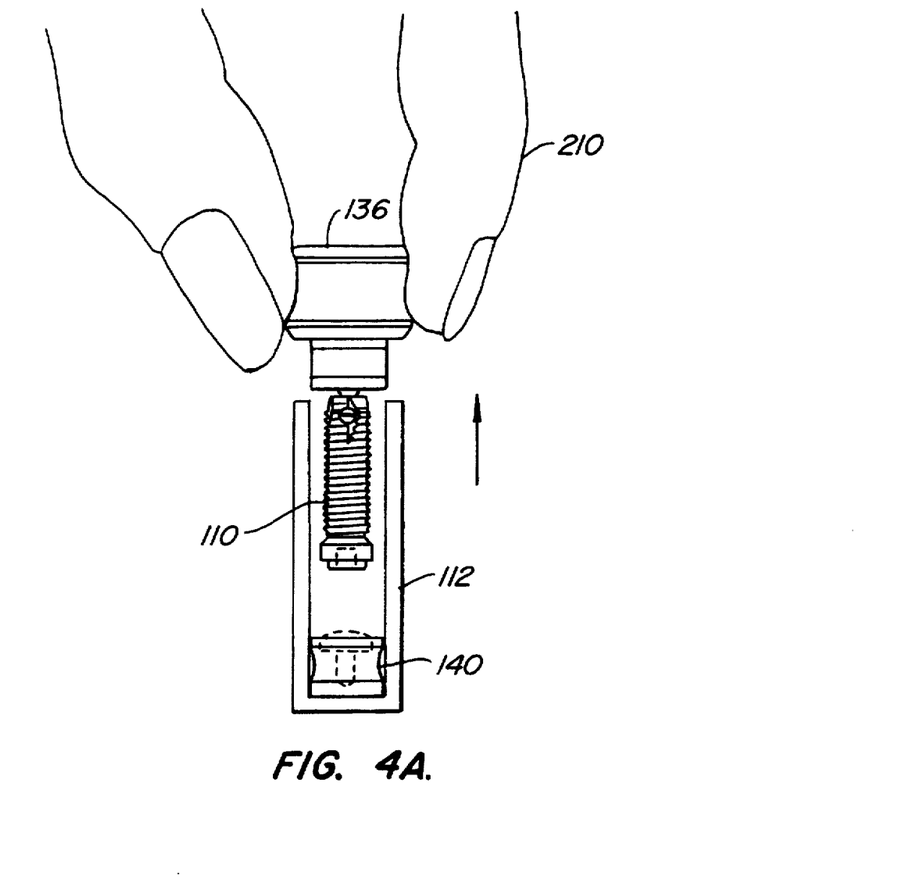
FIGS. 4A–F illustrate a method for delivering a dental implant that is attached to an implant carrier and a cover screw that is housed in a cover screw carrier to a patient according to the present invention.
Figure 4B:
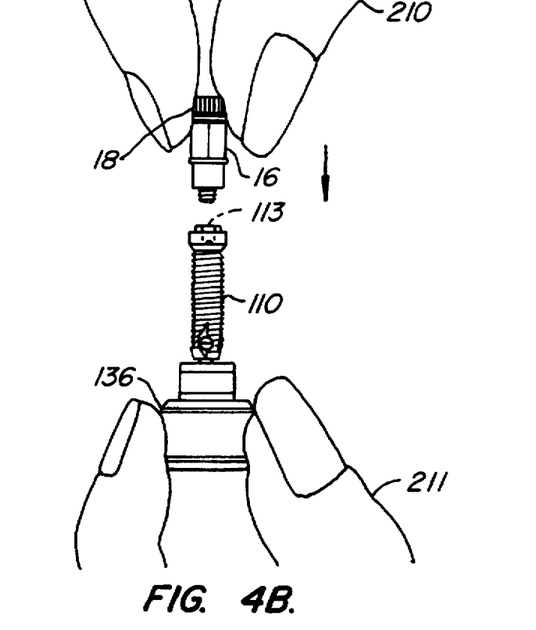
Figure 4C:
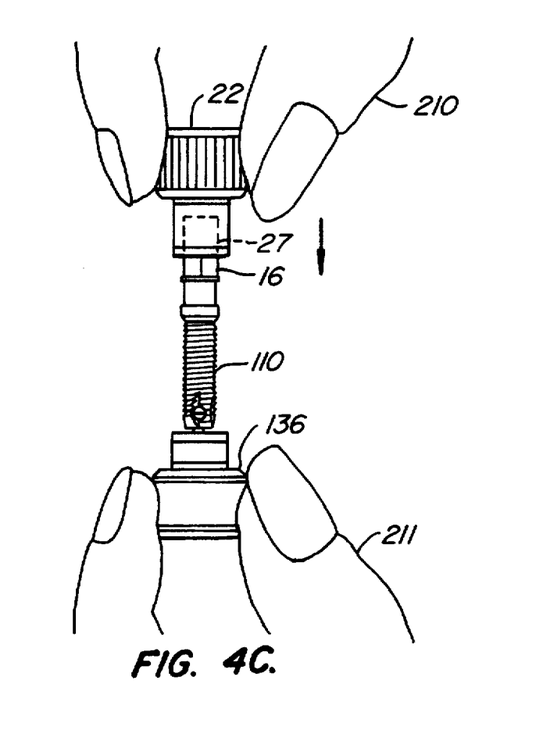
Figure 4D:
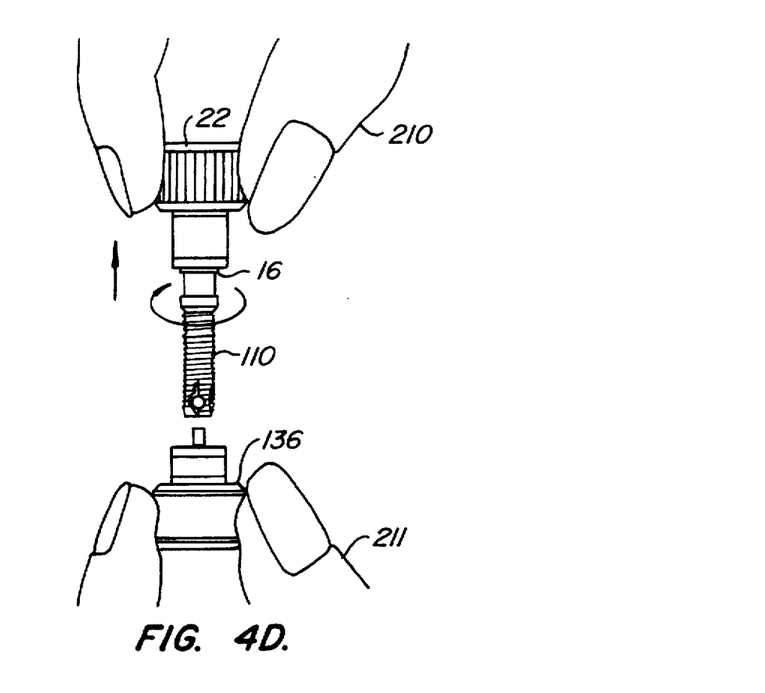

A method for delivering the dental implant 110 and the cover screw 128 of FIG. 2A using the implant mount 16, the implant mount carrier 22, and the cover screw driver 30 of FIGS. 1A and B is illustrated in FIGS. 4A–F. As illustrated in FIG. 4A, to remove the implant 110 from the vial 112, the implant carrier 136 is grasped with one hand 210 and pulled from the vial 112 which is grasped with the other hand 211 (not shown). Once removed, the screw 18 of the implant mount 16 is placed within the female portion 113 of the dental implant 110 and the screw 18 is twisted by hand 210 while the implant 110 is steadied with hand 211 as shown in FIG. 4B. After the implant mount 16 is attached to the dental implant 110, the implant mount carrier 22 is slid over the implant mount 16 by hand 210 while hand 211 remains grasping implant mount 136 so that the top portion of the implant mount 16 is received into the interior portion 27 of the implant mount carrier 22 as shown in FIG. 4C. Implant mount 136 is then removed from the dental implant 110 by grasping implant mount carrier with hand 211 and twisting and/or pulling until the implant mount 136 is detached from the implant 110 while implant mount carrier 22 remains attached to the implant mount 16 as shown in FIG. 4D. The dental implant 110 can then be delivered to the patient as described above.

Figure 4E:
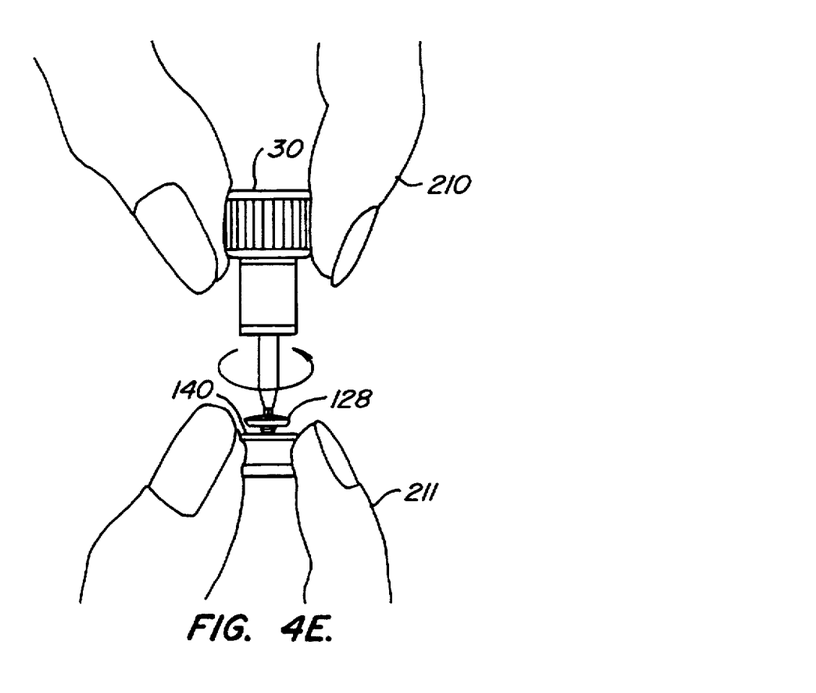
Figure 4F:
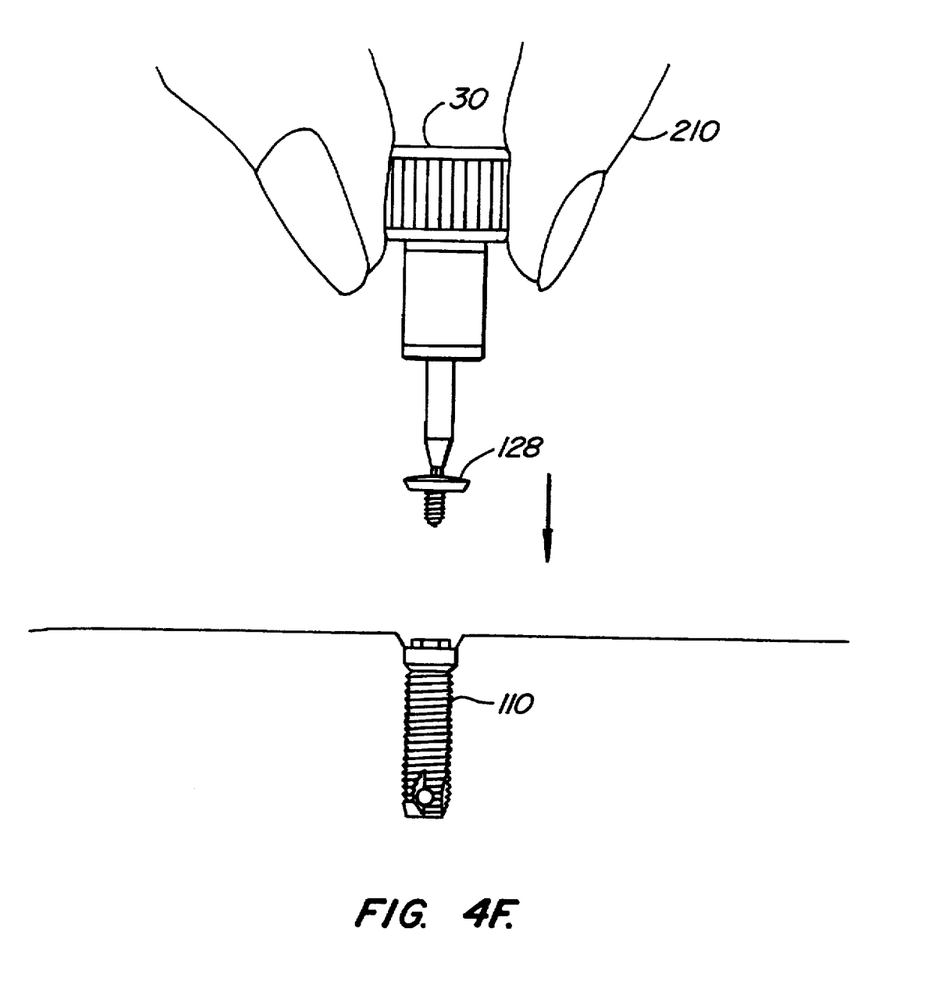

To insert the cover screw 128, the opened vial 112 is lifted to slide out the cover screw carrier 140. Once the cover screw carrier 140 is outside the vial 112, the cover screw carrier 140 is grasped by hand 211 and a cover screw driver 30 is grasped by the other hand 210. The cover screw driver 30 is then press fit with the cover screw 128 as shown in FIG. 4E. The cover screw 128 is then removed from the cover screw carrier 140 by twisting and/or lifting the cover screw driver 30 with hand 210. The cover screw 128 is then delivered to the patient as shown in FIG. 4F.

The invention has now been explained with reference to specific embodiments. Other embodiments will be apparent to those of ordinary skill in the art upon reference to this description. It is therefore not intended that this invention be limited, except as indicated by the appended claims.

What is claimed is:

1. An apparatus in kit form comprising:
   an elongate dental implant having a top end and a bottom end;
   a storage device; and
   an implant carrier removably attached to the bottom end of said dental implant, said implant carrier extending away from the implant so that the top end is not covered by the implant carrier, whereby said dental implant can be removed manually from said storage device by grasping said implant carrier.

2. The apparatus of claim 1, wherein said implant carrier further comprises a first attachment means which is removably attached to said storage device.

3. The apparatus of claim 2, wherein said storage device comprises a container having an opening therein, and wherein said first attachment means comprises a tab extending into said opening of said storage device.

4. The apparatus of claim 3, further comprising:
   a cover screw for insertion into a top end of said dental implant;
   a cover screw carrier for housing said cover screw, said cover screw carrier having means for removable attachment to said storage device;
   wherein said storage device comprises a container having two open ends opposite each other, said implant carrier attached to one of the open ends and said cover screw carrier attached to the opposite end to completely enclose said dental implant and said cover screw within said storage device.

5. The apparatus of claim 3, wherein said tab is circular in cross section, and wherein said container includes a cylindrical interior portion, an open end and a closed end, said tab extending through said open end into said interior portion thereby forming a cover over said open end, whereby said dental implant is completely enclosed within said storage device.

6. The apparatus of claim 5, further comprising:
   a cover screw for insertion into the top end of said dental implant; and
   a cover screw carrier for housing said cover screw.

7. The apparatus of claim 6, wherein said cover screw carrier comprises a substantially cylindrical body with an opening for housing said cover screw, said cover screw carrier being removably housed in said interior portion of said container between said closed end and said dental implant.

8. The apparatus of claim 7, wherein said cover screw carrier and said dental implant are adjacent each other in said container.

9. The apparatus of claim 1, further comprising a second attachment means on said implant carrier for removably attaching said dental implant to said implant carrier.

10. The apparatus of claim 9, wherein said second attachment means comprises a shaft extending from said implant carrier and into said bottom end of said dental implant.

11. The apparatus of claim 10, wherein said dental implant has a cylindrical opening at said bottom end, wherein said shaft is cylindrical and is press fit within said cylindrical opening.

12. The apparatus of claim 10, wherein said cylindrical opening is threaded and wherein said shaft is threaded and mated with said threaded cylindrical opening.

13. An apparatus in kit form comprising:

a dental implant having a top end and a bottom end;

an implant carrier removably attached to said bottom end of said dental implant, said implant carrier extending away from the implant so that the top end is not covered by the implant carrier;

a cover screw carrier;

a cover screw for said dental implant housed in said cover screw carrier; and a storage device for housing said dental implant and said cover screw carrier.

14. The apparatus of claim 13, wherein said implant carrier further comprises a first attachment means removably attached to said storage device.

15. The apparatus of claim 14, wherein said storage device comprises a container having an opening, and wherein said first attachment means comprises a tab extending from said implant carrier and into the opening of said storage device.

16. The apparatus of claim 15, wherein said tab is circular in cross section, and wherein said container includes a cylindrical interior portion, an open end and a closed end, said tab extending through said open end into said interior portion thereby forming a cover over said open end, whereby said dental implant is completely enclosed within said storage device.

17. The apparatus of claim 16, wherein said cover screw carrier comprises a substantially cylindrical body with an opening for housing said cover screw, said cover screw carrier being housed in said interior portion of said container between said closed end and said dental implant.

18. The apparatus of claim 17, wherein said cover screw carrier and said dental implant are adjacent each other in said container.

19. The apparatus of claim 13, further comprising a second attachment means on said implant carrier for removably attaching said dental implant to said implant carrier.

20. The apparatus of claim 19, wherein said second attachment means comprises a shaft extending from said implant carrier and into said bottom end of said dental implant.

21. The apparatus of claim 20, wherein said dental implant has a cylindrical opening at said bottom end, wherein said shaft is cylindrical and is press fit within said cylindrical opening.

22. The apparatus of claim 20, wherein said cylindrical opening is threaded and wherein said shaft is threaded and mated with said threaded cylindrical opening.

23. An apparatus in kit form for delivering dental parts to a patient comprising:

a dental implant having a top end and a bottom end;

an implant mount having a top end and a bottom end, said bottom end of said implant mount being removably attached to said top end of said dental implant;

an implant mount carrier engaged with said top end of said implant mount;

a first storage device having an open interior portion removably engaged with said implant mount carrier such that said dental implant is enclosed within said interior portion of said first storage device, and such that said dental implant can be removed from said first storage device by grasping only said implant mount carrier;

a cover screw for said implant, said cover screw having a head;

a cover screw driver attached to the head of said cover screw; and a second storage device having an open interior portion removably engaged with said cover screw driver such that said cover screw is enclosed within said interior portion of said second storage device, and such that said cover screw can be removed from said second storage device by grasping only said cover screw driver.

24. The apparatus of claim 23, wherein said open interior portion of said first storage device is cylindrical.

25. The apparatus of claim 24, wherein said implant mount carrier further comprises a first attachment means on said implant mount carrier removably attached to said first storage device.

26. The apparatus of claim 25, wherein said first attachment means further comprises a tab having a circular cross section extending from said implant mount carrier and into said open interior portion of said first storage device forming a cover over said first container, whereby said dental implant is completely enclosed within said first storage device.

27. The apparatus of claim 23, wherein said open interior portion of said second storage device is cylindrical.

28. The apparatus of claim 27, wherein said cover screw driver further comprises a second attachment means on said cover screw driver removably attached to said second storage device.

29. The apparatus of claim 28, wherein said second attachment means comprises a tab having a circular cross section extending from said cover screw driver and into said open interior portion of said second storage device forming a cover over said second container, whereby said cover screw is completely enclosed within said second storage device.

30. An apparatus in kit form for delivering dental parts to a patient comprising:

a dental implant having a top end and a bottom end;

an implant mount having a top end and a bottom end, said bottom end of said implant mount being removably attached to said top end of said dental implant;

an implant mount carrier engaged with said top end of said implant mount;

a cover screw for said implant;

a cover screw driver attached to a head of said cover screw; and a storage device having an open interior portion and two open ends, wherein said implant mount carrier is removably engaged with one of the open ends such that said dental implant is enclosed within said interior portion of said storage device, and wherein said cover screw driver is removeably engaged with the other open end such that said cover screw is enclosed within said interior portion of said storage device.

31. A method for delivering a set of dental parts from a storage device to a patient comprising the steps of:

grasping an implant carrier attached to a bottom end of a dental implant to remove said dental implant from said storage device;

attaching an implant mount to a top end of said implant while still grasping said implant carrier;

attaching an implant mount carrier to said implant mount while still grasping said implant carrier; and removing said implant carrier from said dental implant, whereby said implant is available for insertion into the patient.

32. The method of claim 31, further comprising:

removing a cover screw carrier housing a dental implant cover screw from said storage device;

attaching a screw driver to a top end of said cover screw;

removing said cover screw from said cover screw carrier by said screw driver, whereby said cover screw is available for insertion into said dental implant.

33. A method for applying a dental implant delivered from a first storage device to a patient, said dental implant removably connected to an implant mount, said implant mount connected to an implant mount carrier, comprising the steps of:

grasping said implant mount carrier to remove said dental implant from said first storage device;

positioning said dental implant at the desired position on the patient;

applying a torque to the implant mount carrier to screw said dental implant into the patient;

removing said implant mount carrier and said implant mount from said dental implant;

applying a torque to said implant mount to further secure said dental implant after removal of said implant mount carrier;

removing a dental implant cover screw attached to a cover screw driver from a second storage device by grasping said cover screw driver;

positioning said cover screw driver over said dental implant;

applying a torque to said cover screw driver to attach said cover screw to said dental implant; and removing said cover screw driver from said cover screw.

34. An apparatus in kit form comprising:

a dental implant having a top end and a bottom end;

a storage device;

an implant carrier removably attached to the bottom end of said dental implant such that said dental implant can be removed manually from said storage device by grasping said implant carrier; and an attachment means on said implant carrier for removably attaching said dental implant to said implant carrier.

35. The apparatus of claim 34, wherein said attachment means comprises a shaft extending from said implant carrier and into said bottom end of said dental implant.

36. The apparatus of claim 35, wherein said dental implant has a cylindrical opening at said bottom end, wherein said shaft is cylindrical and is press fit within said cylindrical opening.

37. The apparatus of claim 35, wherein said cylindrical opening is threaded and wherein said shaft is threaded and mated with said threaded cylindrical opening.

38. An apparatus in kit form comprising:

a dental implant having a top end and a bottom end;

an implant carrier removably attached to said bottom end of said dental implant;

a cover screw carrier;

a cover screw for said dental implant housed in said cover screw carrier;

a storage device for housing said dental implant and said cover screw carrier;

wherein said implant carrier comprises a first attachment means removably attached to said storage device, wherein said storage device comprises a container having an opening, and wherein said first attachment means comprises a tab extending from said implant carrier and into the opening of said storage device;

wherein said tab is circular in cross section, and wherein said container includes a cylindrical interior portion, an open end and a closed end, said tab extending through said open end into said interior portion thereby forming a cover over said open end, whereby said dental implant is completely enclosed within said storage device; and wherein said cover screw carrier comprises a substantially cylindrical body with an opening for housing said cover screw, said cover screw carrier being housed in said interior portion of said container between said closed end and said dental implant.

39. The apparatus of claim 38, wherein said cover screw carrier and said dental implant are adjacent each other in said container.

40. The apparatus of claim 38, wherein said second attachment means comprises a shaft extending from said implant carrier and into said bottom end of said dental implant.

41. The apparatus of claim 40, wherein said dental implant has a cylindrical opening at said bottom end, wherein said shaft is cylindrical and is press fit within said cylindrical opening.

42. The apparatus of claim 39, wherein said cylindrical opening is threaded and wherein said shaft is threaded and mated with said threaded cylindrical opening.

* * * * *